(12) United States Patent
Herbst (10) Patent No.: US 7,517,311 B1
(45) Date of Patent: Apr. 14, 2009

(54) MODULATION OF PROTEIN PHOSPHORYLATION USING ELECTROMAGNETIC FIELDS

(75) Inventor: Ewa Herbst, Edgewater, NJ (US)

(73) Assignee: Ewa Herbst & Associates, Edgewater, NY (US)

( * ) Notice: Subject to any disclaimer, the term of this patent is extended or adjusted under 35 U.S.C. 154(b) by 0 days.

(21) Appl. No.: 11/633,659

(22) Filed: Dec. 4, 2006

Related U.S. Application Data (63) Continuation of application No. 10/808,989, filed on Mar. 24, 2004, now Pat. No. 7,160,241, and a continuation-in-part of application No. 09/974,542, filed on Oct. 9, 2001, now abandoned.

(60) Provisional application No. 60/476,421, filed on Jun. 6, 2003, provisional application No. 60/238,414, filed on Oct. 6, 2000.

(51) Int. Cl.
*A61N 1/00* (2006.01)
(52) U.S. Cl. ...................................................... 600/13
(58) Field of Classification Search ................ 600/9–15
See application file for complete search history.

(56) References Cited

U.S. PATENT DOCUMENTS

| 5,061,234 A * | 10/1991 | Chaney ....................... 600/14 |
| 6,418,345 B1 * | 7/2002 | Tepper et al. ................. 607/51 |
| 6,561,968 B1 * | 5/2003 | Dissing et al. ................ 600/13 |
| 7,160,241 B1 * | 1/2007 | Herbst ......................... 600/13 |

* cited by examiner

*Primary Examiner*—John P Lacyk
(74) *Attorney, Agent, or Firm*—K&L Gates LLP

(57) ABSTRACT

A method for treating living tissues with electromagnetic fields by subjecting the tissues to be treated with an electromagnetic field that varies as a function of time, and without the need for a corresponding static magnetic field, is provided.

11 Claims, 7 Drawing Sheets

Signal P
Signal r

Signal t

Signal P

Signal r

Signal t

FIGURE 1

Electromagnetic field parameters:

| Signal | 1 | 2 | 3 | 4 | 5 | 6 | 7 | 8=control |
|---|---|---|---|---|---|---|---|---|
| B [mT] | 3 | 3 | 0.5 | 0.05 | 3 | 0.3 | 0.3 | 0 |
| $t_r/t_f$ [us] | 300/20 | 300/50 | 300/50 | 300/50 | 1000/300 | 1000/300 | 300/1000 | |
| f[Hz] | 2 | 2 | 2 | 2 | 2 | 2 | 2 | |

|  | Signal 1 | Signal 2 |
| --- | --- | --- |
| B[mT] | 0.3 | 0.3 |
| $t_r/t_f$[ms] | 1/0.3 | 0.8/0.3 |
| f [Hz] | 2 | 2 |

Example C - Signals

| Signal | Signal Type | Repetition Rate | Bpeak (mT) | dB/dt (mT/s) | Signal Amplitude (Amps) | "Rise" Time (msec) | "Fall" Time (msec) |
|---|---|---|---|---|---|---|---|
| Signal A Channel 1 | Ramp | 2 Hz | 3 | 10/-60 | 7.000 | 0.3 | 0.05 |
| Signal B Channel 7 | Triangle | 2 Hz | 0.3 | 1/-1 | 0.700 | 0.3 | 0.3 |
| Signal C Channel 2 | Ramp | 2 Hz | 0.5 | 1.67/-10 | 1.150 | 0.3 | 0.05 |
| Signal D Channel 6 | Ramp | 2 Hz | 0.05 | 0.17/-1 | 0.115 | 0.3 | 0.05 |
| Signal E Channel 11 | Pulse | 2 Hz | 0.3 | 0.3/-0.3 | 0.700 | 1 | 1 |
| Signal F Channel 12 | Pulse | 2 Hz | 0.05 | 0.05/-0.05 | 0.117 | 1 | 1 |
| Signal G Channel 10 | Ramp | 2 Hz | 0.3 | 1/-0.3 | 0.700 | 0.3 | 1 |
| Signal H Channel 3 | Ramp | 2 Hz | 0.3 | 0.3/-1 | 0.700 | 1 | 0.3 |

FIGURE 7

MODULATION OF PROTEIN PHOSPHORYLATION USING ELECTROMAGNETIC FIELDS

CROSS REFERENCE TO RELATED APPLICATION

This application claims the benefit of U.S. patent application Ser. No. 10/808,989, filed on Mar. 24, 2004, which is hereby incorporated by reference herein in its entirety. U.S. patent application Ser. No. 10/808,989 claims the benefit of U.S. Provisional Patent Application No. 60/476,421, filed on Jun. 6, 2003 and is also a continuation-in-part of U.S. patent application Ser. No. 09/974,542, filed on Oct. 9, 2001, which claims the benefit of U.S. Provisional Patent Application No. 60/238,414, filed on Oct. 6, 2000, all of which are hereby incorporated by reference herein in their entireties.

BACKGROUND OF THE INVENTION

1. Field of the Invention

This invention relates to apparatuses and methods for diagnosing and/or treating tissues/cells using electromagnetic fields, and for determining therapeutically useful electromagnetic fields, and harmful electromagnetic fields.

2. The State of the Art

Electromagnetic fields are used clinically for bone and wound healing and have been used experimentally to enhance nerve repair and/or regeneration. Most investigators have varied a very limited number of electric parameters, usually to show that the biological effect does exist, but without an attempt to optimize this effect. In contrast, the present invention undertakes a systematic approach to evaluate different signals and their components in a complex neuron explant model as a first step toward verification of the in vivo efficacy of such defined EM fields.

There are approximately 500,000 cases of nerve injury of upper extremities per year. Recovery from pain and restoration of function is slow and there is a need for more research in this area to speed up the whole process (Sisken and Walker, 1995).

The EMF signals which have been tested most extensively both in vitro and in vivo are 15 Hz pulse train as well as 72 Hz repetitive single pulse (EBI, Inc., Parsippany, N.J.) and 2 Hz repetitive single pulse (Bietic Research, Inc., Lyndhurst, N.J.) measured as a voltage induced in a small pick-up coil. A 2 Hz/3 Gauss field signal was tested in vivo, resulting in an increased axon elongation (Sisken et al, 1989) in the crushed rat sciatic nerve; the regeneration rate was enhanced by 22%, which is comparable to that reported in the literature with conditioning lesions, growth factors and hormones (Sisken et al, 1993).

In vitro results using 2 Hz/0.5 Gauss EMF on the cultured dorsal root ganglia (DRG) explants showed significantly increased neurite outgrowth (Sisken et al, 1990). DRG explants in culture are a well-established in vitro model to study effects of different factors on nerve regeneration (Greenebaum et al, 1994). The chick DRG has been used as a model testing system for growth factor effects and mechanisms for the past 40 years (Levi-Montalcini, 1968). The dorsal root ganglion is the sensory part of the sensory-motor axis; sensory neurons are in the ganglia whereas motor neurons are in the ventral portion of the spinal cord.

The equipment used most often for in vitro and in vivo studies of low frequency electromagnetic field effects on nerve regeneration was developed originally for bone healing (Electro-Biology, Inc., Parsippany, N.J.) and delivers either a repetitive 72 Hz single pulse or a pulse train with a repetition rate of 15 Hz. Nerve regeneration studies using this equipment were performed by: Ito and Bassett; Orgel et al; and Subramanian et al. The RF signal Diapulse system has also been used for nerve regeneration experiments (Wilson; Raji and Bowden). Some investigators (Blackman; Rusovan et al; Subramanian et al) used various sinusoidal EMFs. A repetitive single pulse system by Bietic Research, Inc. (Lyndhurst, N.J.) has also been used in wound healing and nerve regeneration experiments (Sisken et al; Orgel et al). For review of the above studies, see Sisken (1991).

SUMMARY OF THE INVENTION

In light of the foregoing, one object of this invention is to provide a method for determining therapeutic as well as harmful values of B and/or dB/dt specific to a given cell, tissue type, tissue system (plants), or microorganism (such as, for example, bacteria and yeast). As used herein and in the claims, the term "tissue" refers to all of these cells, tissue types, tissue systems, and microorganisms. The cells, tissue types, and tissue systems can be of any origin, including mammalian. The cells, tissue types, and tissue systems can be in vitro or in vivo.

Yet another object of this invention is to provide an apparatus for delivering a therapeutic B and/or dB/dt to a given cell, tissue type, tissue system (plants), or microorganism (such as, for example, bacteria and yeast). Yet still another object of this invention is to provide an apparatus for delivering a B and/or dB/dt to a given cell, tissue type, tissue system (plants), or microorganism (such as, for example, bacteria and yeast) to affect a change in that tissue's state or function, whether beneficial or detrimental.

A still further object of the present invention is to provide a method for avoiding a harmful value of B and/or dB/dt.

In one embodiment, this invention provides a method for treating living tissues with electromagnetic fields by subjecting the tissues to be treated with an electromagnetic field that varies as a function of time, and without the need for a corresponding static magnetic field.

In another embodiment, this invention provides a method for avoiding harmful values of dB/dt by recording dB/dt values in a given environment, reproducing those values in cells, tissues, tissue system (plants), or microorganism (such as, for example, bacteria and yeast) in vitro and/or in vivo to determine the effects, and if such effects are detrimental, then operating and/or modifying and/or designing the equipment and/or circuitry generating the harmful B and/or dB/dt values in the given environment in a manner that avoids the harmful values.

DETAILED DESCRIPTION OF SPECIFIC EMBODIMENTS

All of the prior art systems described in the Background section above have voltage output stage powering the coils, which makes it difficult to set up experiments in which B (magnetic flux density) and dB/dt (time rate change of B), as well as the shape of the electric field E, which depends on dB/dt, can be well-defined a priori. This is due to the fact that the B field induced inside the coils is a function of the current flowing through the coils and has no linear relationship with the output voltage. Accordingly, in this invention it is preferred to control the current flowing through the coils, thereby avoiding the problems when attempts are made to provide a specified B field by controlling the voltage.

Figure 5:
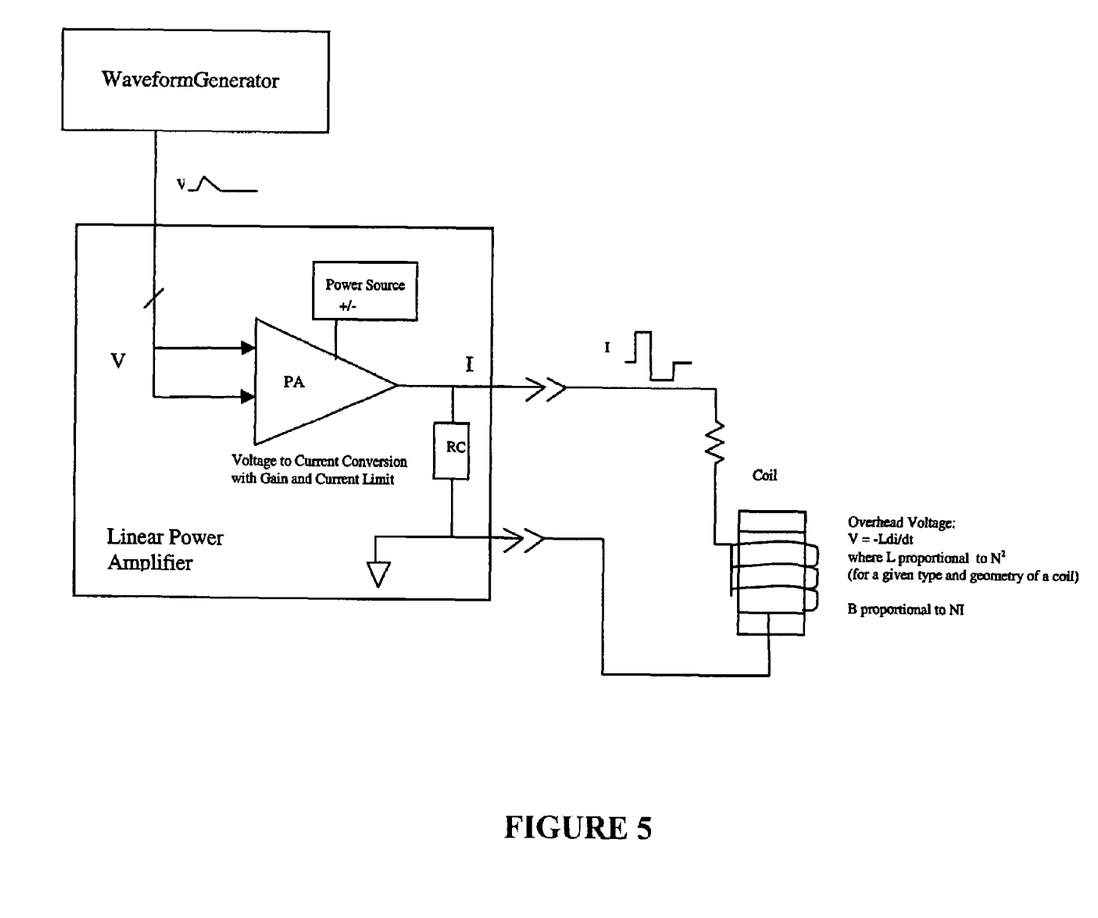
FIG. 5 depicts an illustration of an electromagnetic field generating system in accordance with certain embodiments of the present invention.

In the experiments described herein, the magnetic flux density B is controlled directly by controlling current from an electromagnetic field generating system. One illustration of such a system is shown in FIG. 5. The system also allows for control of dB/dt variations and, consequently, for changing the parameters of the electric field in the treated area in a well controlled manner. Once the geometry and the number of turns of the coils have been specified, B is strictly proportional to the current I with a proportionality constant specific for the coil system used. This allows one to a priori specify B field in the experiments, by specifying current I. By changing one of the parameters (maximum magnetic flux density or its time characteristics) while keeping the other constant, dB/dt can be changed in a controlled way as well.

The impact of various dB/dt rates on both positive and negative biological responses can be of special importance, as the time rate of change of the magnetic flux density may have effect on the cell membranes. The biological responses to electric and/or magnetic fields, and specifically to dB/dt, may influence healing processes in the body, as well as cell damage, depending on the levels and timing characteristics of the signals involved. To our knowledge, no systematic study has been performed to evaluate dB/dt effects on biological processes, specifically on cell growth, tissue healing and/or regeneration. Cell growth can be assessed, for example, by the measurement of neurite outgrowth. An example of a biological process that can be assessed is, for example, the amount of myosin phosphorylation.

As electric and magnetic fields cannot be separated from each other and investigated independently, it is difficult to find a suitable model for studying their respective influence on biological tissue. One such approach is to investigate effects of electric field in vitro at the different radial distances from the center of a culture dish (Misakian et al, 1990, Bassen et al 1992) in a presence of identical magnetic flux density throughout the whole surface area of the dish. In the center of the dish the induced electric field is equal to zero and it reaches its maximum at the edge of the dish. The resulting current density j is equal to the conductivity of the media $\sigma$ times the electric field E: $j=\sigma E$. In earlier experiments by Sisken et al (1984), the resulting current density for 15 Hz pulse train signal (EBI, Parsippany, N.J.) was 5 $\mu A/cm^2$ at the distance of 2 cm from the center of the dish. By placing DRGs at various specified distances from the center of the dish, the biological effects of electric fields of various amplitudes on DRGs can be studied in the presence of the same magnetic flux density. This approach allows one to differentiate biological effects due to the electric field only, as it increases proportionally to the distance from the center of the dish, while all other EMF parameters and culture conditions remain equal.

For a true Helmholtz coil, the magnetic flux density B on the coil axis at half the distance between the coils is: $B=\mu_o NI/1.4a$; wherein $\mu_o$ is permeability for a vacuum, N is the number of turns of each coil, I is the current flowing through each coil, and a is the coil radius equal to the distance between the coils. Once the geometry and the number of turns of the coils have been specified, B is strictly proportional to the current I with a proportionality constant specific for the coil system used. This allows one to a priori specify B field in the experiments, by specifying current I. By changing one of the parameters (maximum magnetic flux density or its time characteristics, for example) while keeping the other constant, dB/dt can be changed in a controlled way as well. In addition to Helmholtz coils, various other coil geometries, such as a saddle, a helix, or the like as are presently used can be used for this invention, and optionally multiple coils and/or coil geometries can be used in this invention.

To be able to answer questions about signal specificity, several electrical parameters have to be investigated, one at a time, in a consistent and logical order. These parameters include, without limitation: type (shape) of the signal; signal amplitude, signal frequency; for pulses, a single pulse or pulse train; time characteristics of the pulse, time rate of change of magnetic flux density, etc. Both amplitude of the field induced in the tissue and time characteristics of the signal are of importance, while discussing kinetics of biological responses at the cell membrane.

The present invention is not limited to the use of a preferred current output system (current output amplifier), as long as the above signal considerations are taken into account.

Signal Generator and Power Amplifier of the Invention

Figure 1:
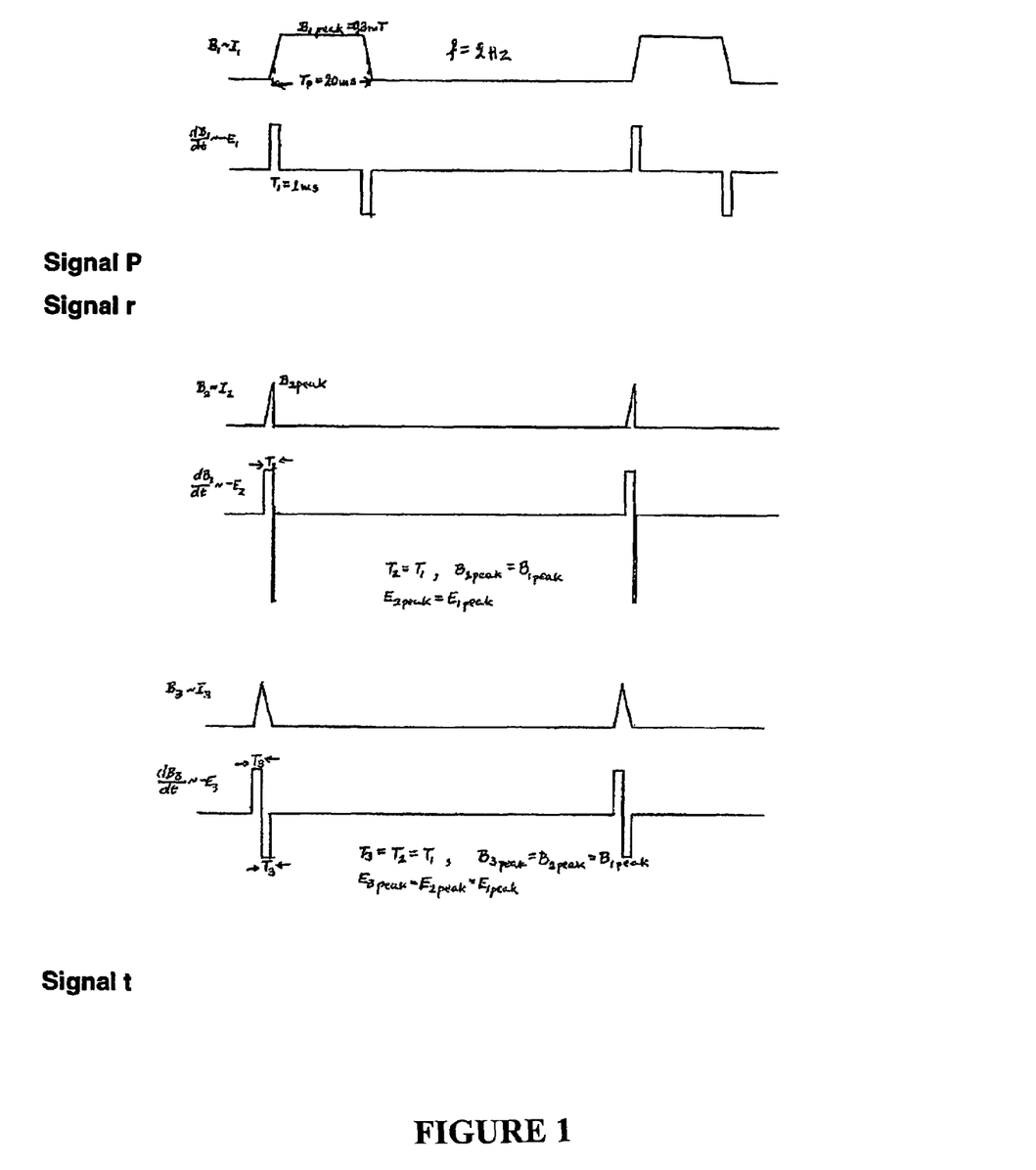
FIG. 1 depicts three different electromagnetic field signals that may be used in accordance with certain embodiments of the present invention.
Figure 6:
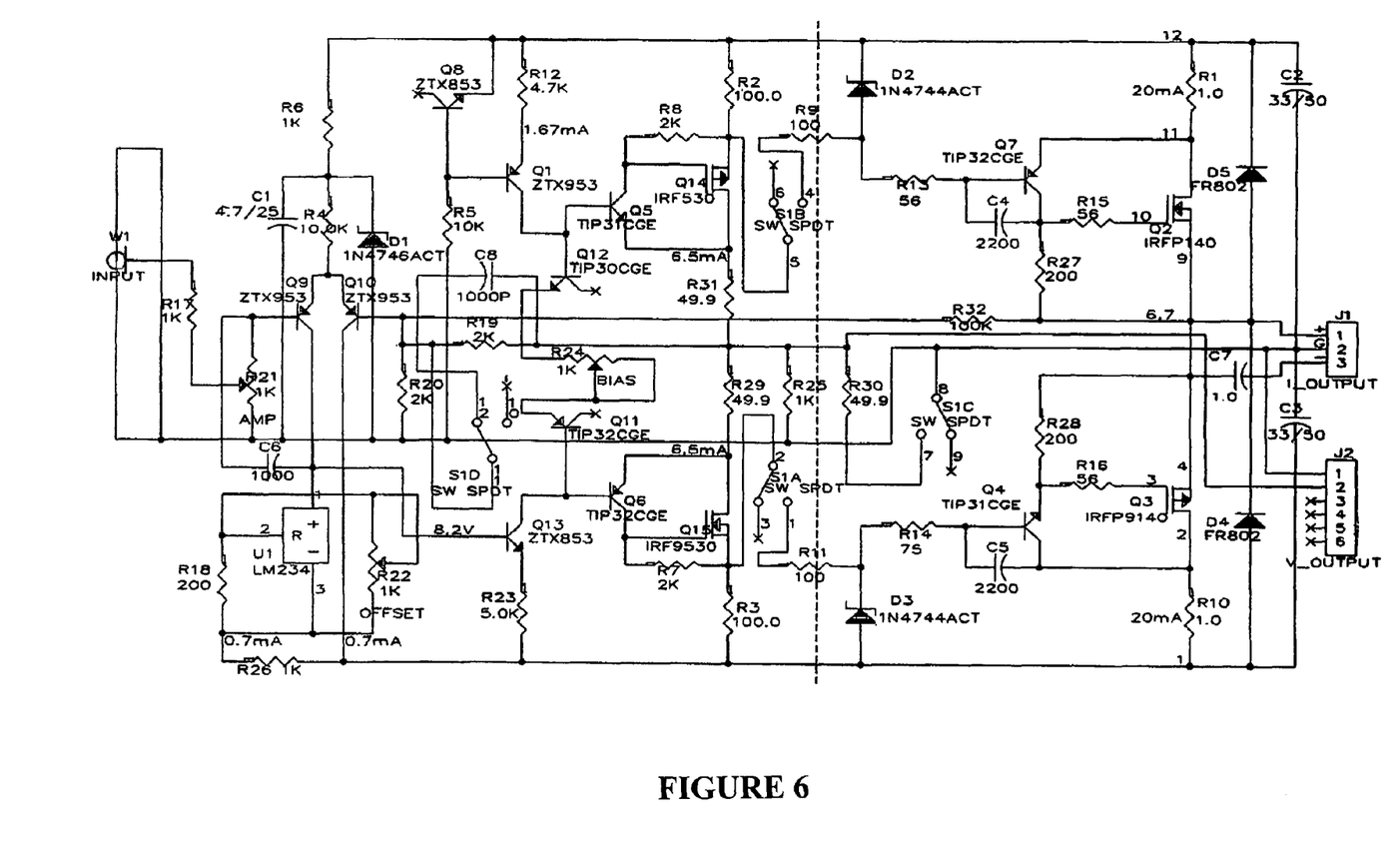
FIG. 6 depicts an illustration of an amplifier that may be used in accordance with certain embodiments of the present invention.

The microprocessor-controlled signal generator for three specific signals (FIG. 1), which were used in the experiments described below, is designed around an AM186ES 40-MHZ microcontroller. A suitable signal generator is disclosed in U.S. Pat. No. 6,029,090, the disclosure of which is incorporated herein by reference. The chosen signal is fed into a current output power amplifier, such as one with peak output currents in the range of about ±50 A, a maximum output voltage of up to a few thousand volts, and with a bandwidth of up to a few megahertz. The amplifier can have a built-in inductance load over-voltage protection, as well as a current limit for the current amplifier and an open-load protection. It can be used with resistive and capacitive loads, in addition to inductive loads such as the coils of this invention. As set forth above, the present invention is not limited to the use of a specific amplifier as long as the signal conditions set forth herein are taken into account. An example of one amplifier that may be used in accordance with the present invention is shown in FIG. 6.

The resulting stimulator system preferably incorporates safety features that protect the equipment from damage if the coil is not attached when the power is turned on. The current output power amplifier allows the opportunity to define a priori, and to accurately control, the magnetic flux density B, which is directly proportional to the current, as well as the time derivative of the magnetic flux density dB/dt and the resulting electric field E. A primary consideration with the development of the stimulator's universal power amplifier for generating signals useful in this invention is that it is preferably both linear and fast, in order to take care of all the different signals. Additionally, it is preferably able to deliver a wide range of currents, depending on the type of the signal and its time characteristics and amplitude, as well as the size of the coils. Depending on the current and the inductance of the coil/s, the voltage available at the output of the stimulator may vary significantly.

Coil of the Experimental Setup

The following description uses a Helmholtz coil configuration in some embodiments, although other coil configurations can be used instead, if more appropriate for a specific application. For the experiments described herein, the coil design had to take into account both the bandwidth of the signal and a requirement for not increasing the temperature at the culture site. The number of turns of the coil wire depends on the optimal solution for the whole stimulator system with respect to minimum and maximum current amplitudes permitted in the coils as well as the bandwidth of the signal. A desirable maximum temperature increase at the treatment site of less than 0.5° C., due to the heat development in the coils, provided a limitation on the maximum current allowed; in fact, the final design of the coil used in these experiments exceeded the inventor's own specifications, and resulted in a temperature increase in the culture media in the middle of the coil system of less than 0.1° C. for less than 0.75 A of current.

Two sets of rectangular Helmholtz-type coils (30 cm×30 cm) were designed and built. In order to use the coils in the future under various experimental conditions, each half of the Helmholtz coil consisted of two 33-turn coils. Such a design allows for four different system configurations: in series to double the number of turns and limit current and power dissipation in the coils; in parallel to decrease the inductance and increase the bandwidth of the Helmholtz coils; not connected at all and used as a 33-turn Helmholtz coil system; or not connected and powered by two identical current sources, with current in each 33-turn Helmholtz coil system flowing in the opposite direction to cancel the field inside the Helmholtz coil.

In these experiments, both halves of the Helmholtz coils were connected in series to assure the same current from the current-output stage of the power amplifier. Great care was taken to design a coil system that could be used for both higher and lower frequencies, thus taking into account a skin effect at higher frequencies and power dissipation in the coils at lower frequencies.

A Litz wire NELCL50/36SPDN-1 (New England Electric Wire Corporation, Lisbon, N.H.) was used for coil manufacturing in one embodiment of the experimental setup. This wire, which is recommended for frequencies 20-50 kHz, was sufficient for the initial experiments from a frequency point of view. Ideally, a coil bandwidth higher than the given power amplifier's bandwidth is desirable, which can be achieved with a higher frequency Litz wire.

A compromise was struck in terms of a desirable equivalent AWG (i.e., an equivalent wire diameter), due to the fact that a larger-diameter wire would not fit under the incubator's door for the present experimental setup. To compensate for the smaller diameter AWG used, as well as the resulting increase in energy dissipation and a potential heating of the wire, a larger number of turns was required. Since the frequency was not critical for the initial experiments, the coils in each half of the Helmholtz configuration were connected in series, resulting in a 66-turn coil, and thus minimizing the current into the system. The total DC resistance of the Helmholtz coil, including the connecting wires to the stimulator, was measured at 2.4 Ohms.

Applications of the Method and Apparatus of the Invention

Although the experiments described below represent a special case, peripheral nerve regeneration in vitro, the invention is not limited to the peripheral nerve regeneration. Examples of other application areas are, without limitation: cancer treatment; cell/tissue growth, repair and/or regeneration; growth, repair and/or regeneration of the central nervous system; effects on the autonomous nervous system; wound healing; other soft tissue healing and/or repair; tendon repair; cartilage repair; bone healing and/or repair; positive and negative effects on immune system function; disinfecting solid, liquid, and gas media; as well as other physiological, cellular, and biochemical effects. Yet other applications may include design of power stations and other work places, as well as machinery and instruments, to prevent harmful effects of high-level transients, due to switching of electric and/or magnetic fields. In addition, effects on plant development, growth, and function and/or on their pests and/or symbionts can be achieved, such as by burying coils in the soil (preferably powered by solar radiation, and optionally with batteries storing the solar power for release into the coils at the appropriate time).

Depending on the application, the electrical as well as timing and/or frequency parameters of both the magnetic flux density B and its time derivate dB/dt will have different usable ranges. For example, to stimulate healing and/or regenerative processes in living tissues, the magnetic flux density ranges are likely between the geomagnetic field up to about 10 mT, depending on the type of the tissue and whether the effects are sought in a cell culture, a small animal (such as a rat or cat), or a larger animal (such as a human or horse). The harmful effects of B and/or dB/dt may likely also start within this range, again depending on the type of the tissue and the size of the living organism and will continue for higher fields and/or dB/dt. The timing parameters alone may be of importance, as well as being a defining factor for the value of dB/dt and the resulting peak electric field E, which is a function of dB/dt. The frequency range for the beneficial effects may be from the low Hz range up to 100 kHz or higher, and may be up to the MHz range for some specific applications and combinations with specific field amplitudes. In most cases it will be under 10 kHz. This again may depend on the application area and the type of the organism treated. The frequency ranges for harmful effects will typically start within 100 kHz range and go up—again it may depend on the combinations of B and the timing characteristics of the signal employed.

EXPERIMENTS USING METHOD AND APPARATUS OF THE INVENTION

Tissue Cultures

The chick embryo nervous system was used to test for neurite-promoting activities of EMFs in culture. (Sisken et al., 1990; Greenebaum et al., 1996.) In these tests, sensory parent neurons of typical peripheral nerves (i.e., dorsal root ganglia (DRG) sensory neurons) were cultured. DRG dissected from 8½- to 9-day chick embryos were explanted to 60-mm culture dishes coated with rat tail collagen. Explants, rather than single cells, were used to determine the effects on neurite growth since the presence of the highly important non-neuronal cells in close approximation to neurons was maintained.

Six dishes/groups with 12 DRG per dish were used in each experiment; one group served as a sham control and one as an EMF exposed group. Both groups were matched to have comparable concentrations of nerve growth factor (NGF)

added. The NGF concentrations used were 0 ng/cc, 2 ng/cc, and 50 ng/cc (with two dishes per each concentration), to look at the effects of EMFs at low versus high NGF concentrations. The cultures were fed with neurobasal and N2 supplement (Gibco Co., NY). They were cultured for 48 hours at 37° C. and 95% air, 5% $CO_2$, before fixation with phosphate-buffered formalin.

DRG Preparation

Under sterile conditions, 8½- to 9-day-old chick embryos were obtained and placed in phosphate-buffered saline (PBS) with pen/strep added. The embryos were then dissected under a dissecting microscope at low power. The DRG were then explanted from the embryos and placed in Falcon 60-mm-diameter culture dishes. A slight film of media was present on the bottom of the dishes to aid in the adhesion of the DRG to the bottom of the dishes.

The DRG were positioned in the culture dishes at two different radial distances from the center of the dish. Four DRG were placed at about 5 mm from the center and the other eight on the circle at 20 mm from the center. This approach gave a four-fold difference in the amplitude of the induced electric field, as well as in the current density. A total of 12 dishes were used per experiment (6 controls, 6 treated). The dishes were placed in an incubator for 2 hr before the remaining media was added. This was done to further promote DRG adhesion to the bottom of the dishes. After this 2-hr period, NGF and media were added to the appropriate dishes. At this time, in order to keep the evaluators blinded, the code used in this experiment was written on top of both dish covers.

Experimental Set-Up

Each experiment was run for two consecutive days, with cultures exposed to EMFs for two hours/day, and was repeated seven to eight times, to assure enough data for statistical analysis.

All six EMF-treated culture dishes were placed on one shelf, centrally located in a 30 cm×30 cm Helmholtz coil housed in the bottom chamber of a two-chamber incubator. The other six dishes (controls) were placed in the top incubator. The coil was placed parallel to the bottom of the culture dishes, resulting in an induced B field perpendicular to the surface of the dish. This arrangement guaranteed identical magnetic fields in each dish, and was confirmed by measurement.

The coils were designed in such a way that a maximum temperature increase at the culture site, due to the heat development in the coils, would be less than 0.5° C. The temperature was monitored during the experiments with a non-metal, alcohol thermometer placed in front of the coil, and checked also in a spare dish with culture media inside the coil (it was measured to be less than 0.1° C. for the current amplitude of 0.75 A used in the experiments). The temperature inside the culture dishes was not monitored during the experiments due to contamination risk.

Coils in the experimental system were connected to the EMF stimulator outside the chamber, consisting of the microprocessor-controlled signal generator and a current output power amplifier with peak output current in the range of ±10 A, a maximum output voltage of up to ±50 V, and with a bandwidth of 50 kHz. A suitable amplifier is shown in FIG. 6.

The evaluation was handled in a blinded fashion by an independent statistician. Only the person who handled the exposure system and measured the fields daily knew which coil was active and what field was applied. This person did not evaluate the results.

Three different signals were tested sequentially, ratherthan in parallel, since access to three independent incubators was not possible; however, the evaluation of the results was done at the same time. All electrical parameters were measured during each experiment using a small search-coil attached to an oscilloscope to measure an induced electric field and a magnetometer to measure the ambient field. The magnetometer was also used to calibrate the system by comparing its reading to the calculated value of B, based on the value of current flowing through the coils. Once the calibration factor was defined, the measurement of current in the coils was sufficient to define the B field.

Electromagnetic Fields Tested

The efficacy of three electromagnetic fields (FIG. 1) on nerve regeneration in vitro was compared in a feasibility study. The peak magnetic flux density was constant for all three fields and equal to 0.3 mT.

The first field tested was a square pulse magnetic field ($B_{1peak}$=0.3 mT, pulse width=20 ms, repetition rate=2 Hz), imitating the electrical parameters of the Bietic Research, Inc. system that showed positive effects on nerve regeneration in vivo in the crushed sciatic nerve in rats (Sisken et al, 1989). The dB/dt for Bietic Research 2 Hz/0.3 mT field, based on the inventor's calculations using measured values of the voltage induced in the search coil, was in the range 0.32 T/s to 0.54 T/s, depending on the rise or fall time of the B field.

For these experiment with a square pulse magnetic field, both rise and fall times were set to approximately 1 ms, which is in the range of the original Bietic Research signal (0.9-2 ms). This results in dB/dt=0.3 T/s, E=−0.03 V/m at the 2 cm distance from the center of the dish, and j=0.51 $\mu A/cm^2$. This first experiment sought to define if the field amplitude, which affects the nerve regeneration in vivo in a rat sciatic nerve model, would also be effective in vitro. If not, lower signal amplitudes were to be used, as earlier experiments showed that 0.05 mT has been effective in vitro (Sisken, 1990).

The additional two fields tested (FIG. 1) had their electrical parameters modified in such a way that additional preliminary data could be obtained to indicate appropriate experimental directions for the Phase II investigation. In both cases both the rise time and the positive dB/dt were identical to those in the first signal. In signal r the fall time was about 2.5 times shorter, resulting in a higher negative dB/dt. Signal t had symmetrical rise and fall times of 1 ms.

Evaluation Methods

Assessment of Neurite Outgrowth. DRG evaluation began by taking pictures using a 33-mm SLR camera (with no lenses), mounted directly to a microscope. Color-print film was used. The microscope objective was at 4× magnification, which meant that more than one picture had to be taken of larger DRG. Once the film was developed, the multiple pictures were assembled into a montage for each DRG. It should be noted that a total magnification factor of 46 was present when the measurements were made. This magnification factor was determined using a calibrated microscope slide by taking pictures under the same magnification and developing and printing the photographs under the same procedures.

From these pictures, DRG neurite length (i.e, the distance measured in a straight line from the main body of the DRG to the tip of each neurite) and the number of neurites per DRG were determined. Length measurements were made on each quadrant using a metric rule with 1-mm divisions. The main body of the DRG, containing the neuronal cell bodies, was easily distinguishable and outlined free-hand with a permanent marker. The mean neurite length for each DRG was also calculated.

Measurements were made using a jeweler's large magnifying glass, so that both picture and ruler were magnified simultaneously. The observer then measured the distance from each neurite tip to the outline of the DRG main body, calling out the length measurements and recording them on a tape recorder. The neurite number was then simply a matter of recording the number of neurite length measurements for each DRG.

Tape-recorded measurements were then input into computer and analyzed using SAS (Statistical Analysis System). All of the measurements were made in a blinded fashion, by a technician who was not involved in culturing the DRG or in treating the DRG with EMFs.

Statistical Analysis. Mean neurite length and mean number of neurites was computed for each location (inner and outer DRG) in each dish. Then a series of linear mixed models (Verbeke and Molenberghs, 1997) was fitted to these data. A mixed model was used because there are two sources of variability in this experiment: the first is dish-to-dish variability, while the second is within-dish variability. A separate mixed model was used for each of the three signals. In each model, the between-dish factors were: NGF concentration, which appeared at three levels (labeled 1 (0 ng/cc), 2 (2 ng/cc), and 3 (50 ng/cc)); treatment, which appeared at two levels (the active signal versus control labeled as t and c); and the interaction between concentration and treatment. The within-dish fixed-effects factor was location in the dish (inner versus outer DRG labeled as I and O) and all two-factor and three-factor interactions between location and concentration and/or treatment.

Also, an analysis was conducted to compare signals by pooling the data into a larger mixed model, which incorporated signal as another fixed factor in the between-dish effect (as well as interactions with all of the above stated fixed effects). Finally, in all these mixed models, day of experiment (labeled as R for replicate) was treated as a blocking factor. Statistical significance for all main effects and all interaction effects was set at 0.05. If a main effect or an interaction among these effects was statistically significant, then post hoc comparison of mean response was based on Fisher's least significant difference procedure; this was facilitated by using least squares means. All arithmetic was done using Procedure Means and Procedure Mixed in SAS.

Results

For neurite length and signal r there is a significant effect due to the interaction of treatment and concentration. Post hoc comparison of means shows that the mean response to the signal r is larger than the mean response for control at the 2nd concentration (P=0.0002) but there is no difference between treatment and control at the remaining two concentrations. The following table shows the magnitude of the effects.

TABLE 1 mean neurite length (in parenthesis standard error) for signal r and comparison to its control

| | concentration | | |
|---|---|---|---|
| treatment | 1 | 2 | 3 |
| signal r | 0.633 (0.035) | 1.040 (0.032) | 0.858 (0.033) |
| control | 0.668 (0.032) | 0.864 (0.032) | 0.834 (0.032) |
| P value | 0.47 | 0.0002 | 0.61 |

For neurite length and signal r there is also a difference between the mean response for inner versus outer DRG, where the mean response for inner 0.849 (±0.019) is significantly larger than the mean response for outer 0.782 (±0.019) with P=0.013.

Discussion

A highly significant difference in the neurite length (P=0.0002) for one signal, with respect to its control (at an NGF concentration of 2 ng/cc), but not for the other two signals, indicates that there may possibly be a signal-dependent effect on mean neurite length in the DRG model. Additionally, the fact that the mean neurite length for inner DRG was larger than for the outer DRG would indicate a possibility that the electric field induced in the outer ring was too high for an optimal biological response. This could possibly explain a lack of results with a pulsed B field, which gave a response in an earlier study. We used an amplitude of 0.3 mT taken from an in vivo experiment. In a previous in vitro experiment, the amplitude was 6 times lower. Also the time of the original experiment was longer, which can possibly have an impact on the outcome.

FURTHER EXAMPLES

Example A

EMF Effects on Neurite Outgrowth Determined by Three Different Assessments

Digital imaging techniques were used to assess the effects of a previously tested electromagnetic field (EMF); see Herbst et al., (2002) Abstract Book BEMS 24th Annual Meeting, Quebec City, Canada, which is hereby incorporated by reference in its entirety; on the neurite outgrowth in a chick embryo dorsal root ganglia (DRG) model.

Dorsal root ganglia (DRG) dissected from 9-day-old chick embryos were explanted to 60 mm culture dishes coated with rat tail collagen and cultured, as known in the art. See, for example, B. F. Sisken et al (1990) Restor. Neurol. Neurosci, 1:303-309, which is hereby incorporated by reference in its entirety. Eight DRGs were placed on a 10 mm circle from the center of each culture dish. The cultures were fed with neurobasal and B27 supplement (Gibco Co., New York) and cultured for 48 hours at 37° C. and 95% air, 5% $CO_2$. Each experiment had 6 dishes in the EMF treated group and 6 dishes in the sham control group. Three concentrations of NGF were used (0 ng/ml, 1.67 ng/ml, and 5 ng/ml) with 2 dishes per NGF concentration. The signal applied was a ramp with a peak magnetic flux density B of 0.3 mT with a repetition rate of 2 Hz. It had a rise time of 0.85 ms and fall time of 0.3 ms which corresponded to a dB/dt of 0.35 T/s and −1.0 T/s respectively. The EMF was induced in a Helmholtz coil (30 cm×30 cm, 66 turns) powered by a current-output power amplifier (Herbst Research, Inc., Edgewater, N.J.) with a bandwidth of 50 kHz, max available current of 10 A and a voltage compliance of 50 V, see Herbst et al (2002) Abstract Book BEMS 24th Annual Meeting, Quebec City, Canada. The EMF was applied for 2 hours/day for 2 days. After 48 hours, digital images of each DRG were obtained using a high-resolution digital camera (Redlake MASD ES1.0 MegaPlus). See P. P. Resig et al (2002) Poster BEMS 24th Annual Meeting, Quebec City, Canada, which is hereby incorporated by reference in its entirety. Each experiment was repeated 12 times, resulting in up to 192 DRGs for each concentration in both treated and control groups for a possible maximum of 1,152 DRGs in the whole study. Assessment of neurite outgrowth was performed with the Quantlm digital image analysis program (Zedec Technologies, Morrisville, N.C.). See P P Resig et al (2002) Abstract Book BEMS 24th Annual Meeting, Quebec City, Canada and A Shah et al (1998) Abstract Book BEMS 20th Annual Meeting, St Pete, Fla., both of which are incorporated by reference in their entirety. The length of each neurite, the number of neurites and the total neurite area were obtained for each DRG. Statistical analysis was performed using a linear mixed model. Post hoc comparison of mean responses was based on Fisher's least significant differences procedure. Statistical significance was determined at the 0.05 level.

An EMF treatment effect at an NGF concentration of 5 ng/ml was seen for the number of neurites (18.7% increase, p=0.01) as well as the neurite area (16.7% increase, p=0.029). A somewhat weaker response was seen for the mean neurite length (less than 10% increase, p=0.046). There was no EMF effect indicated for any of the measured parameters at the NGF concentrations of 0 ng/ml or 1.67 ng/ml.

These results support previous findings as disclosed in Herbst et al (2002) Abstract Book BEMS 24th Annual Meeting, Quebec City, Canada regarding the effect of this particular signal on neurite outgrowth in this model. In addition, the digital imaging and analysis techniques were demonstrated to be effective in quantifying the neurite outgrowth. Furthermore, the added measurement of total neurite outgrowth area, see A Shah et al (1998) Abstract Book BEMS 20th Annual Meeting, St Pete, Fla., may be a more meaningful parameter for determining the biological response to EMF.

Example B

An EMF System for Biological Experiments

An EMF stimulation system is disclosed that includes a signal generator, a power amplifier and a coil. To control both the shape and the amplitude of the magnetic field a current output amplifier is used. The amplifier has a voltage compliance (i.e. highest voltage available on the output) being at least equal to the voltage generated in the coil at the frequencies of interest. This prevents the signal from being clipped or distorted. The voltage generated in the coil depends on the inductance of the coil, current through the coil, and frequency of the signal. Thus, the coil inductance is taken into account for each particular set of experiments. This inductance is proportional to $N^2$ (where N is the number of turns of the wire in the coil) and to geometry of the coil. Consequently, for a given type of the coil (e.g. a Helmholtz coil or a solenoid) and for specific coil dimensions, the generated voltage is proportional to $N^2$. As the B field is proportional to both the current and the number of turns, the maximum B field desired also influences the system design.

B is proportional to NI; v=−Ldi/dt, where L is proportional to $N^2$ (for a given type and geometry of the coil).

Once the current and the maximum frequency of the signal are defined, an appropriate coil wire can be chosen. The wire has a gauge appropriate for the current magnitude and takes into account maximum allowable heat dissipation in the coil and the maximum allowable temperature increase at the experimental site. For low frequencies, a copper wire may be appropriate, while for higher frequencies and shorter pulses a Litz wire can be selected to counter any skin effects (current flowing only on the surface of the wire).

Two systems for two different inductive loads were developed. The two systems have a digital current control. The output voltage of each system can be increased further by providing a larger power supply.

The first system was designed for experiments, for example, on neurite outgrowth in a chick DRG model, which includes a Helmholtz coil (($\phi$=15.2 cm, N=44 turns, L=1.34 mH at 100 kHz), a digitally controlled signal generator (Herbst Research, Inc., Edgewater, N.J.) and a power amplifier (modified LVC5050, AE Techron Inc., Elkhart, Ind.). The system can generate fields with a rise/fall time down to 55 µs at B=3 mT, resulting in dB/dt of 55 T/s. Higher fields can be generated for slower signals as long as the relationship v=−Ldi/dt is satisfied. This system is not limited in its applications to neurite outgrowth.

The second system was designed for experiments, for example, on EMF effects on functional recovery in a rat sciatic nerve crash model. The system includes a digitally controlled signal generator and a two-channel current output power amplifier (Herbst Research, Inc., Edgewater, N.J.) with one solenoid per channel ($\phi$=14 cm, N=98 turns, L=376+/−3 µH at 100 kHz), containing a rat cage. Lower coil inductance allows us to run two matched experiments from each amplifier. The rise/fall time can be as low as 55 µs at B=3 mT. This system is not limited in its application to rat sciatic nerve crash model.

Both systems can be pre-programmed with up to 12 signals, selectable by a user with a rotary switch. This allows for blinded experimental conditions. Both systems have also switchable signal settings for two different coils, e.g., a Helmholtz coil and a solenoid. If an experiment requires additional signals later on, they can be downloaded to the signal generator through an external port mounted in the equipment chassis and be functional immediately. The above systems are not limited to 12 signals nor to two different coil settings, more signals and settings can be preset in the system as desired.

Example C

Signal Screening for EMF Effects on Neurite Outgrowth in a Chick DRG Model

Figure 7:
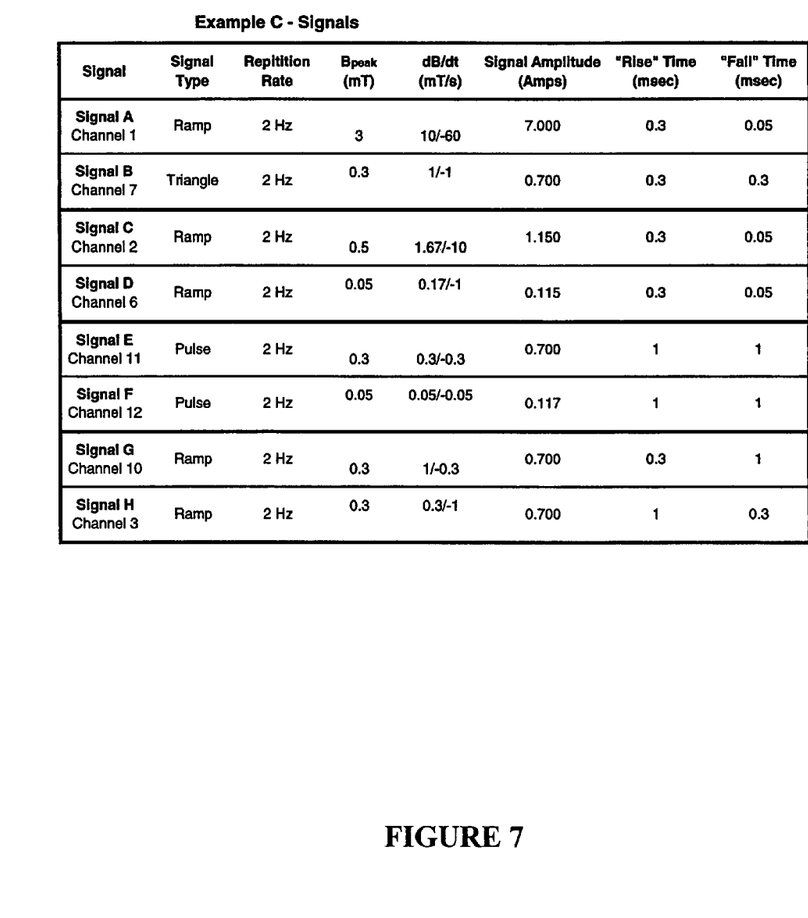
FIG. 7 depicts characteristics of signals generated in an experiment in accordance with one embodiment of the present invention.

A signal generator (Herbst Research, Inc., Edgewater, N.J.), connected to a current output power amplifier (modified LVC5050, AE Techron Inc., Elkhart, Ind.) generated various EMFs in a 44 turn, 15.2 cm Helmholtz coil, placed in an incubator. A magnetic flux density B including ramp, triangle, and/or pulse signal shapes with a repetition rate of 2 Hz, rise and fall times varying from 55 µs to 1 ms, and B varying from 50 µT to 3 mT. The resulting dB/dt varied from 50 mT/s to 55 T/s. The signals generated in this experiment are shown in FIG. 7.

Dorsal root ganglia (DRGs) were dissected from 9-day-old chick embryos and explanted to 60 mm culture dishes coated with rat tail collagen and cultured, as known in the art. See, for example, B. F. Sisken et al (1990) *Restor. Neurol. Neurosci*, 1:303-309, which is hereby incorporated by reference in its entirety. Eight DRGs were placed on a 10 mm circle from the center of each culture dish. Eight EMFs were tested in four experimental series, with two EMFs tested in the same day. Each EMF experiment consisted of 6 dishes in the treated group and 3 dishes in the sham control group and was repeated 6 times. The total number of DRGs used per experiment was 288 in each treatment group and 144 in each control group. Both the EMF-treated and the sham control groups had the same concentration of NGF (5 ng/ml). In all experiments, the cultures were fed with neurobasal and N2 supplement (Gibco Co., New York) and cultured for 48 hours at 37° C. and 95% air, 5% $CO_2$. EMF was applied for 2 hours/day for 2 days, after which time digital images of each DRG were obtained with a high-resolution digital camera (Redlake MASD ES1.0 MegaPlus). See P. P. Resig et al (2002) Abstract Book BEMS 24th Annual Meeting, Quebec City, Canada. Assessment of neurite outgrowth for each DRG was performed with the Quantlm digital image analysis program (Zedec Technologies, Morrisville, N.C.) See P. P. Resig et al (2002) Abstract Book BEMS 24th Annual Meeting, Quebec City, Canada and A J Shah et al (1998) Abstract Book BEMS 20th Annual Meeting, St. Pete, Fla., U.S.A., herein expressly incorporated by reference in its entirety. A linear mixed model was used to evaluate the mean neurite area in each experiment. Statistical significance was determined at 0.05 level. In the absence of significant F test, a Bonferroni adjustment for comparison of each active treatment to its control was made at the 0.025 level.

One out of eight EMF fields tested (a 3 mT ramp with 0.3 ms rise time and 55 μs fall time) had a significant effect on the neurite outgrowth (P=0.016), even after adjustment for multiple comparisons.

This study is a continuation of our two earlier studies E. Herbst et al (2002) Abstract Book BEMS 24$^{th}$ Annual Meeting, Quebec City, Canada, which is hereby incorporated by reference in its entirety. We have in this study systematically tested 8 different EMFs, by changing either B or rise or fall time, one parameter at a time (rise and fall times are defined here as the time for a B field to go from zero to $B_{peak}$, or vice versa). A total of 3,456 DRGs were used in the study.

Example D

Myosin Phosphorylation Experiments

The myosin phosphorylation is a well established experimental model. It's use for evaluation of biological effects of different magnetic fields was first proposed by Shouvalova L A, Ostrovskaja M V, Sosunov E A, Lednev V V (1991), "Weak magnetic field influence of calmodulion-dependent myosin phosphorylation of myosin in solution" in the Dokladi Academy of Science USSR 217: 227-231, which is hereby incorporated by reference in its entirety.

The method was further improved by M. S. Markov with respect to optimization of the reagent rate and especially the reading of the results of the assay—from gel electrophoresis to Cherenkov emission. It was used in several experiments. See, for example the Markov references cited below, which are hereby incorporated by reference in their entirety.

Figure 2:
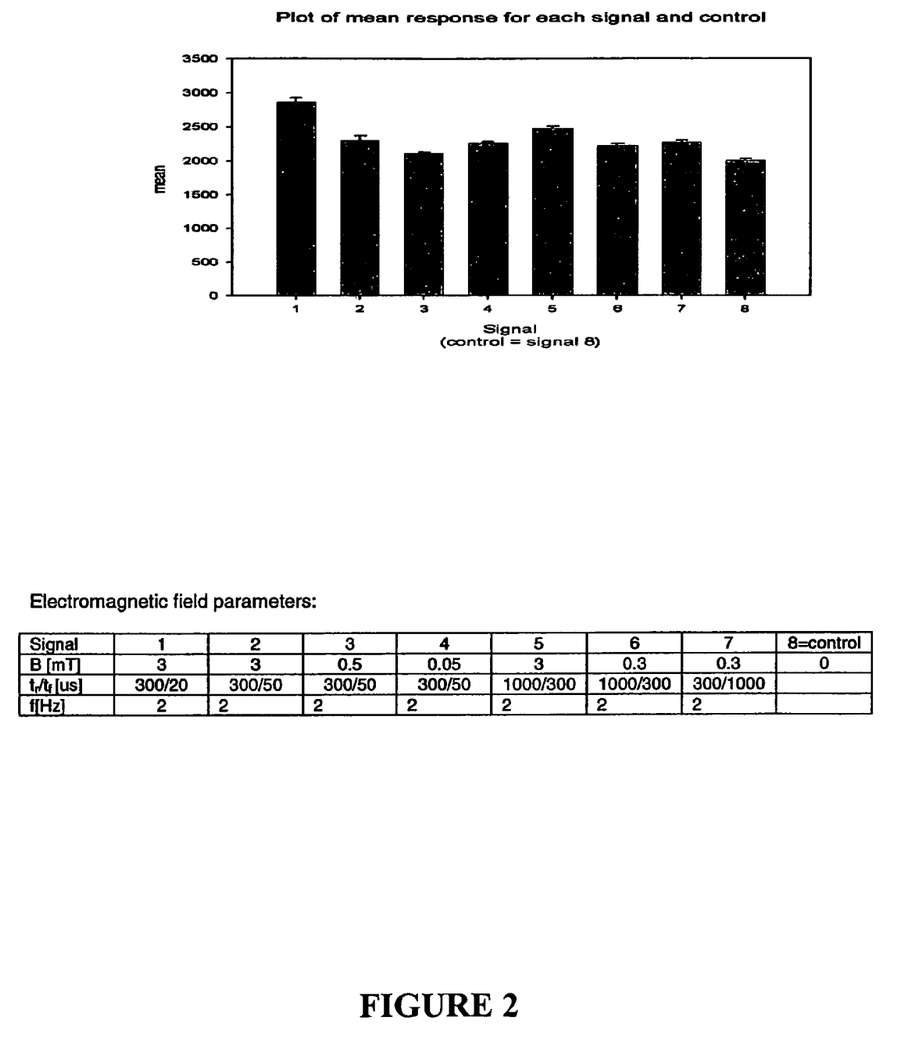
FIG. 2 depicts results of an experiment in accordance with certain embodiments of the present invention.

We have performed three experiments using M. S. Markov's experimental model. In the first experiment the electromagnetic fields tested had parameters previously described in Example C (Signals A, C, D, G, and H—see FIG. 7) with two additional fields added (ramps: B=3 mT; repetition rate 2 Hz; $t_r/t_f$ 300 μs/20 μs, and 1 ms/300 μs respectively). Due to a small sample volume, a special solenoid was used with a diameter of 22 mm, length of 38 mm, and 95 turns. This allowed using a lower power amplifier than in Example C. The results and corresponding electrical parameters for experiment 1 are shown in FIG. 2.

Figure 3:
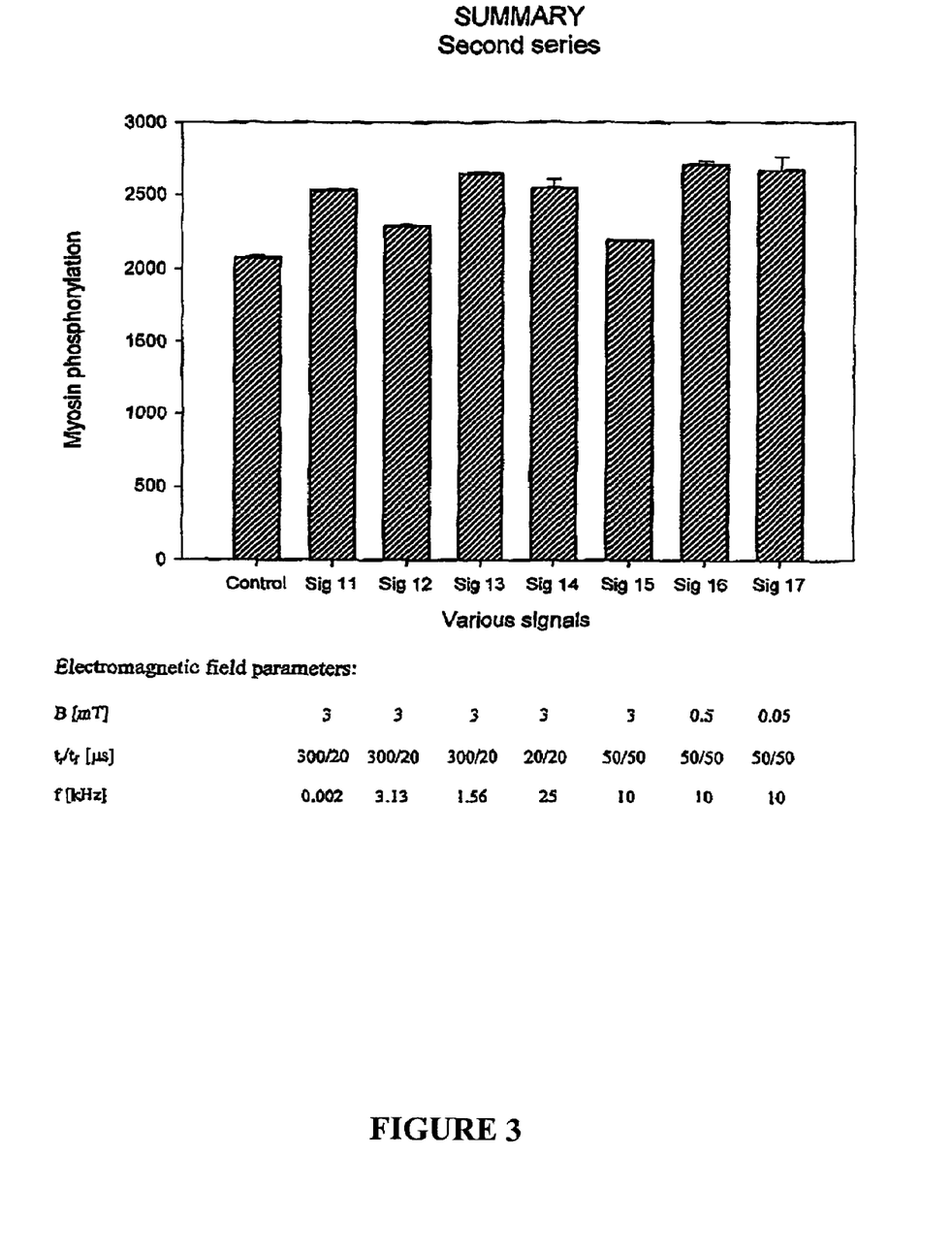
FIG. 3 depicts results of an experiment in accordance with certain embodiments of the present invention.

In the second experiment, we have used the most effective signal from the first experiment and added six new signals (see FIG. 3) to screen for even more effective signal in this model. The solenoid has been modified (made longer, new length 53 mm) to increase the length of the uniform field. This required the increase of the number of turns to 127. The experimental results and corresponding electrical parameters for experiment 2 are shown in FIG. 3.

The results of both experiments show that myosin phosphorylation can be modulated by the electromagnetic fields. This methodology can be used for influencing a number of biochemical and biological processes.

Figure 4:
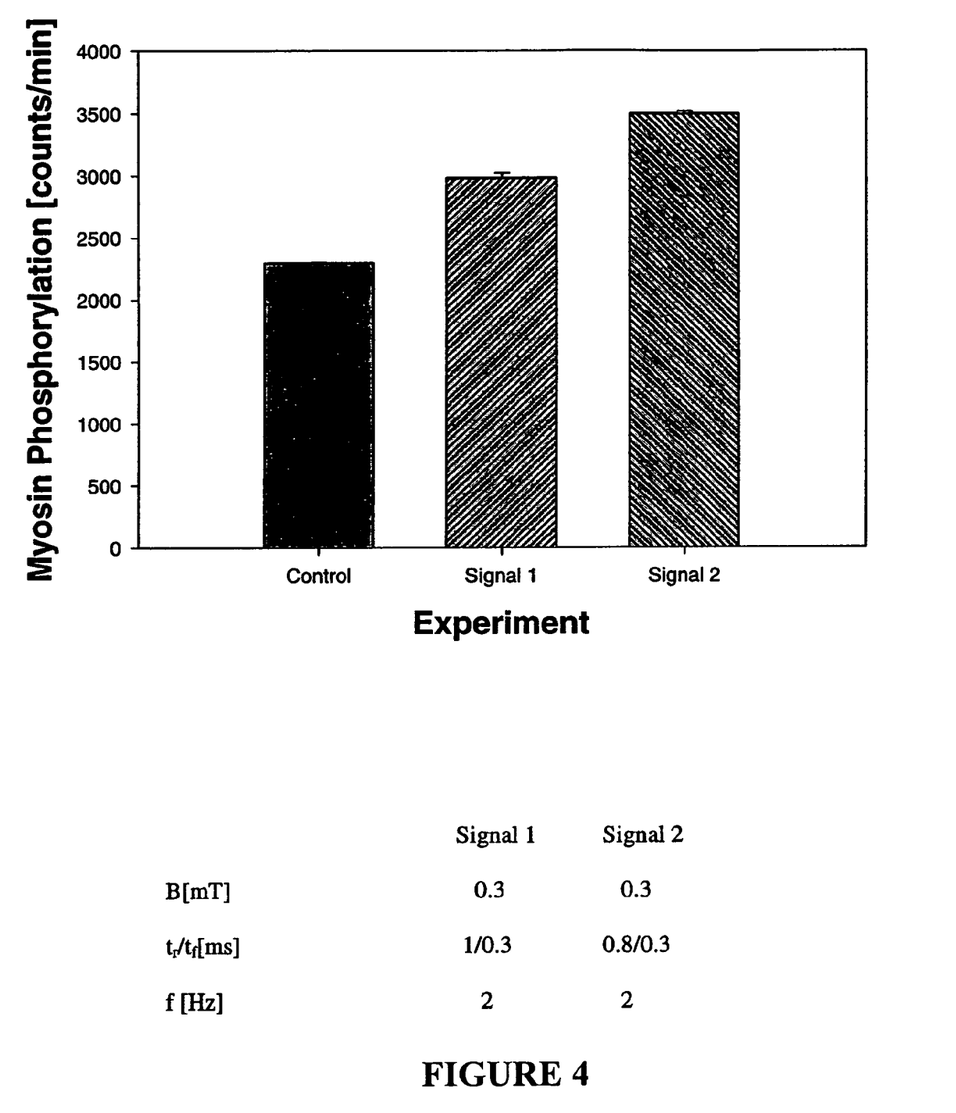
FIG. 4 depicts results of an experiment in accordance with certain embodiments of the present invention.

The third experiment was performed to evaluate effects of two similar signals (ramps: B=0.3 mT; repetition rate 2 Hz; $t_r/t_f$ 1 ms/300 μs, and 0.8 ms/300 μs respectively) generated by two different systems (consisting of different signal generators, power amplifiers, and coils) from Example A and Example D-experiment 2. The results and corresponding electrical parameters for experiment 3 are shown in FIG. 4. Signal 1 was generated by a system described in Example D-experiment 2, while Signal 2 was generated by a system described in Example A. The experiments were conducted over two days, three series in each day. Each series included control, Signal 1, and Signal 2; in total, six repeats.

Experiment 3 was conducted using two specially designed chambers, which had to maintain matching temperature at the level of 37±0.5° C. during the 5-min exposure. For Signal 1 the Eppendorf tube with the working solution was immerged in a specially designed cylindrical container which was filed with water at 37° C. For signal 2 the samples were placed in another custom made chamber which maintains the 37±0.1° C. by constant perfusion of water pre-warmed by passage through a Fisher Scientific model 900 heat exchanger. Temperature was monitored with a Fisher Scientific Traceable Thermometer. This chamber was constantly used in all previous experiments published by Dr. Markov and coworkers.

Three different control samples were run each day at different conditions: controls 1 and 4 were run in a plastic cylinder filled with water at 37° C. Controls 2 and 5 were run with the same container placed inside the cylindrical coil which delivers signal 1 (the coil was not powered). Control 3 and 6 were run inside standard temperature chamber. This approach to controls was taken in order to be sure that the improvised temperature chamber (for Signal 1) and standard temperature chamber (for Signal 2) provide similar conditions with respect to control assays. The values for control samples 1,2,3 were very close and the same was seen for controls 4,5,6. This is convincing evidence that even if small changes in the temperature in chamber 1 occur they do not influence myosin phosphorylation course.

The results show a significant difference between the effects of those two signals tested on myosin phosphorylation. This difference can be a result of different bandwidth of the two electromagnetic field generating systems with resulting different harmonics content. Signal 2 was generated by a lower bandwidth amplifier.

REFERENCES

The following documents in their entirety are expressly incorporated by reference herein:

Bassen, H., Litovitz, T., Penafiel, M. and R. Meister. ELF in vitro exposure systems for inducing uniform electric and magnetic fields in cell culture media. Bioelectromagnetics 13:183-198, 1992.

Greenebaum, B, Sutton, Carl, M Subramanian Vadula, J H Battocletti, T Swiontek, J DeKeyser, and B F Sisken. Effects of pulsed magnetic fields on neurite outgrowth from chick embryo ganglia. Bioelectromagnetics 17: 293-302, 1996.

Herbst, E. Response of rat skin flaps to sinusoidal electromagnetic fields. Proceedings of the 9th Annual Conference of the IEEE Engineering in Medicine and Biology Society, vol. 9:75-76, 1987.

Herbst, E. Multifunctional Electric and/or Electromagnetic Stimulator. Proceedings of the Second World Congress for Electricity and Magnetism in Biology and Medicine, June 1997.

Levi-Montalcini, Rand Angeletti, P U 1968. Nerve growth factor. Physiol. Rev. 48:534-569.

Misakian, M. and W T Kaune. Optimal experimental design for in vitro studies with ELF magnetic fields. Bioelectromagnetics 11:251-255, 1990.

Shah, A. J., C. Fischer, C. F. Knapp and B. F. Sisken. Determination of neurite outgrowth of dorsal root ganglia using image processing. Proceedings of the 20$^{th}$ Annual Meeting of the Bioelectromagnetics Society, June 1998.

Sisken, B F, B. McLeod and A A Pilla. PEMF, direct current and neuronal regeneration: effect of field geometry and current density. J. Bioelectricity, 3:81, 1984

Sisken, B F, M Kanje, G Lundborg and E Herbst. Stimulation of rat nerve regeneration with pulsed electromagnetic fields. Brain Research 485:309, 1989.

Sisken, B F, M Kanje, G Lundborg, and Kurtz, W. Pulsed electromagnetic fields stimulate nerve regeneration in vitro and in vitro. Restor. Neurol. and Neurosc. 1:303-309, 1990.

Sisken, B F. Electric and pulsed electromagnetic field effects on nerve tissue regeneration. In: Electromagnetics in Medicine and Biology. Eds C Brighton & S Pollack, San Fran. Press, pp 259-274, 1991.

Sisken, B F, J Walker and M Orgel. Prospects on Clinical Applications of Electrical Stimulation for Nerve Regeneration. J Cellular Biochem. 52: 404-409, 1992.

Sisken, B F and J. Walker. Therapeutic aspects of electromagnetic fields for soft tissue healing. Chapter in Electromagnetic Fields: Biological Interactions and Mechanisms In: The Amer. Chemical Society Series 250, Editor Martin Blank, Amer. Chem. Soc., Washington D.C. 1995.

Subramanian M, C Sutton, B Greenebaum and B F Sisken. Interaction of pulsed electromagnetic fields and nerve growth factor on nerve regeneration in vitro. In: Electromagnetics in Medicine and Biology. (Eds.) C Brighton and S Pollack, San Francisco Press, 145-152, 1991.

Verbeke, G. and Molenberghs, G. *Linear Models in Practice*, Springer Verlag, 1997.

Walker, J, J M Evans, P Resig, S Guarnieri, P Meade and B F Sisken. Enhancement of functional recovery following crush lesion to the rat sciatic nerve by exposure to pulsed electromagnetic fields. Exper. Neurol. 125: 302-305, 1994a.

Walker J L, Evans J M, Meade P, Resig P, Sisken B F: "Gait-Stance Duration as a Measure of Injury and Recovery in the Rat Sciatic Nerve Model" Journal of Neuroscience Methods 52:47-52, 1994b.

Walker J L, Resig P, Guarnieri S, Sisken B F, Evans J M: "Improved Footprint Analysis Using Video Recording to Assess Functional Recovery Following Injury to the Rat Sciatic Nerve", Restorative Neurology and Neuroscience 6:189-193, 1994c.

Zienowicz, R J, B Thomas, W Kurtz and M Orgel. A multivariate approach to the treatment of peripheral nerve transaction injury: the role of electromagnetic field therapy. Plastic and Reconstr. Surgery, 87: 122-129, 1991.

U.S. Pat. No. 6,029,090. Entitled: Multi-Functional Electrical Stimulation System.

U.S. Published Patent Application No. 2002/0143365. Entitled: Multi-Functional Electrical Stimulation System.

U.S. Pat. No. 6,021,347. Entitled: Electrochemical Treatment of Malignant Tumors.

U.S. Published Patent Application No. 2001/0021868. Entitled: Electrochemical Treatment of Tissues, especially Tumors.

U.S. patent application Ser. No. 09/974,542. Entitled: Treatment of Living Tissues Using Electromagnetic Fields.

Shouvalova L A, Ostrovskaja M V, Sosunov E A, Lednev W (1991), "Weak magnetic field influence of calmodulion-dependent myosin phosphorylation of myosin in solution" in the Dokladi Academy of Science USSR 217: 227-231

Markov M. S., Ryaby J. T., Kaufman J. J., Pilla A. A. (1992) Extremely weak AC and DC magnetic fields significantly affect myosin phosphorylation. in "Charge and field effects in Biosystems III", Birkhauser, Boston, 225-230

Markov M. S., Ryaby J. T., Wang S., Pilla A. A. (1992)—Modulation of myosin phosphorylation rates by weak (near ambient) DC magnetic fields—in Proceedings of 18th Annual Northeast Bioengineering Conference, Kingston, R.I., March 1992; IEEE, New York, 63-64

Markov M. S., Wang S., Pilla A. A. (1992)—Weak (ambient range) DC magnetic fields affect myosin phosphorylation in a cell-free preparation—Proceedings of 14th International Conference of the IEEE Engineering in Medicine and Biology Society, Paris, Oct. 29-Nov. 1, 1992; v.14 (1992) 302-303

Markov M. S., Wang S., Pilla A. A. (1992)—Effects of weak low frequency and DC magnetic fields on myosin phosphorylation in a cell-free preparation—Bioelectrochemistry and Bioenergetics 30: 119-125

Markov M. S., Pilla A. A. (1993)—Ambient range sinusoidal and DC magnetic field affect myosin phosphorylation in a cell-free preparation—Electricity and Magnetism in Biology and Medicine, M Blank (ed) San Francisco Press Inc. 323-327

Markov M., Pilla A. A. (1994)—Modulation of cell-free myosin light chain phosphorylation with weak low frequency and static magnetic fields—On the Nature of Electromagnetic Field Interactions with Biological Systems, A. H. Frey (ed.), R. G. Landes Co. Austin Tex., 127-141

Markov M. S., Pilla A. A. (1994)—Static magnetic field modulation of myosin phosphorylation: calcium dependence in two enzyme preparations—Bioelectrochemistry and Bioenergetics 35 (1994) 57-61

Markov M. S., Muesham D. J., Pilla A. A. (1994)—Modulation of cell-free myosin phosphorylation with pulsed radio frequency electromagnetic fields—Charge and Field Effects in Biosystems-4, World scientific M J Allen, S F Cleary, A E Sowers (eds) 274-288

Muehsam D. J., Markov M. S., Muehsam P. A., Pilla A. A., Ronger Sen, Yi Wu (1994)—Effects of Qugong on cell-free myosin phosphorylation: preliminary experiments—Subtle Energies (1994) v.5., # 1, 93-106

Pilla A A, Muehsam D J, Markov M S—A Larmor Precession-Dynamical Model for µT Range Magnetic Field Bioeffects: Water Dipole Orientation and Ion Binding—Proceedings of XVIII Annual International Conference of IEEE Society of Engineering in Biology and Medicine, Amsterdam 1996, ISBN 90-91005-9

Markov M. S., Pilla A A (1997)—Weak static magnetic field modulation of myosin phosphorylation in a cell-free preparation: Calcium dependence—Bioelectrochemistry and Bioenergetics 43: 233-238

Pilla A A, Muehsam D J, Markov M S (1997)—A Dynamic system/Larmor Precession Model for weak magnetic field bioeffects: Ion binding and orientation of bound water molecules—Bioelectrochemistry and Bioenergetics 43: 239-249

Pilla A A. Musham D J, Markov M S, Sisken B F (1999)—EMF signals and ion/ligand binding kinetics: prediction of bioeffective waveform parameters—Bioelectrochemistry and Bioenergetics 48: 27-34

Markov M S, Pilla M (1999)—Static µT-level magnetic fields modulate myosin phosphorylation via kinetic effects on calcium binding to calmodulin—in (F. Bersani, ed) Electricity and Magnetism in Biology and Medicine—Kluwer Academic/Plenum Publishers, New York 605-608.

Pilla M, Muehsam D J, Markov M S (1999)—A Larmor precession/dynamic system model allows µT-range magnetic field effects on ion binding in the presence of thermal noise—In: (F. Bersani, ed) Electricity and Magnetism in Biology and Medicine—Kluwer Academic/Plenum Publishers, New York, 395-399.

Pilla A A, Muehsam D J, Markov M S, Sisken B F (1999)—EMF signals and ion/ligand binding kinetics: prediction of bioeffective waveform parameters—In (F. Bersani, ed) Electricity and Magnetism in Biology and Medicine—Kluwer Academic/Plenum Publishers, New York, 391-394.

Pilla A A, Muehsam, D J, Markov M S (2000)—Time-varying and static magnetic fields in therapeutic applications: a unified theory for weak EMF bioeffects—Millennium International Workshop on Biological effects of electromagnetic fields, Crete, Greece, 330-337, ISBN # 960-86733-0-5113.

Markov M S (2002) Can cell-free myosin phosphorylation be used as a tool for biological dosimetry?—International J. Bioelectromagnetism 4 (2) 163-164

Engstrom S, Markov M S, McLean M J, Holcomb R R, Markova J M (2002)—Effects of non-uniform static magnetic fields on the rate of myosin phosphorylation—Bioelectromagnetics 23:475-479

What is claimed is:

1. A method for modulating protein phosphorylation with electromagnetic fields, comprising:
   providing a signal generator capable of generating a plurality of signals;
   selecting at least one output signal from the plurality of possible signals;
   controlling magnetic flux density (B) by generating a controllable current using said selected output signal;
   applying magnetic flux density (B) to a protein; and
   subjecting the protein to be phosphorylated to a controllable magnetic flux density (B) and dB/dt.

2. The method of claim 1, wherein dB/dt is controllable by controlling magnetic flux density (B), while keeping time (t) constant.

3. The method of claim 2, wherein magnetic flux density (B) is controllable by controlling at least one of the amplitude and timing parameters of the current delivered to a coil for applying the magnetic flux density to the protein.

4. The method of claim 1, wherein dB/dt is controllable by controlling time (t), while keeping magnetic flux density (B) constant.

5. The method of claim 1, wherein dB/dt is controllable by controlling both magnetic flux density (B) and time (t).

6. The method of claim 1, wherein the method further comprises providing a sawtooth magnetic flux density (B) and applying the sawtooth magnetic flux density (B) to the protein.

7. The method of claim 6, wherein the sawtooth magnetic flux density (B) has symmetrical rise and fall times.

8. The method of claim 6, wherein the sawtooth magnetic flux density (B) has asymmetrical rise and fall times.

9. The method of claim 1, wherein dB/dt is controllable by controlling a current input to the means for applying magnetic flux density to the protein.

10. The method of claim 9, wherein the current is provided by the output of a current output amplifier.

11. A method for modulating protein phosphorylation with electromagnetic fields, comprising:
    providing a signal generator capable of generating a plurality of signals;
    selecting at least one output signal from the plurality of possible signals;
    providing the at least one output signal to a power amplifier;
    generating electromagnetic fields using the power amplifier output;
    applying the electromagnetic fields to a protein; and
    subjecting the protein to be phosphorylated to a controllable magnetic flux density (B) and dB/dt.

* * * * *